US012345788B2

(12) United States Patent
Basser

(10) Patent No.: US 12,345,788 B2
(45) Date of Patent: Jul. 1, 2025

(54) MRI TRACTOGRAPHY BASED TRANSIT TIME DETERMINATION FOR NERVE FIBERS

(71) Applicant: The United States of America, as represented by the Secretary, Department of Health and Human Services, Bethesda, MD (US)

(72) Inventor: Peter J. Basser, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 878 days.

(21) Appl. No.: 17/306,841

(22) Filed: May 3, 2021

(65) Prior Publication Data

US 2021/0270921 A1   Sep. 2, 2021

Related U.S. Application Data

(63) Continuation of application No. 14/345,219, filed as application No. PCT/US2012/055458 on Sep. 14, 2012, now Pat. No. 10,996,303.

(60) Provisional application No. 61/535,851, filed on Sep. 16, 2011.

(51) Int. Cl.
*A61B 5/055* (2006.01)
*A61B 5/00* (2006.01)
*G01R 33/56* (2006.01)
*G01R 33/563* (2006.01)

(52) U.S. Cl.
CPC .......... *G01R 33/5608* (2013.01); *A61B 5/055* (2013.01); *A61B 5/40* (2013.01); *G01R 33/56341* (2013.01)

(58) Field of Classification Search
None
See application file for complete search history.

(56) References Cited

U.S. PATENT DOCUMENTS 7,643,863 B2   1/2010   Basser et al.
7,834,627 B2   11/2010  Sakai et al.
(Continued)

OTHER PUBLICATIONS

Over Alexander et al. (Orientally invariant indices of axon diameter and density from diffusion MRI, Neuro-Image 52 (2010), 1374-1389) (Year: 2010).*
(Continued)

*Primary Examiner* — Shahdeep Mohammed
*Assistant Examiner* — Marjan Saboktakin
(74) *Attorney, Agent, or Firm* — Leydig, Voit & Mayer, Ltd.

(57) ABSTRACT

Magnetic resonance methods comprise tractographically establishing a path along a structure in a specimen and finding a distribution of structure radii or cross-sectional areas along the path. Based on the distribution and the path, end-to-end functional characteristics of the structure are estimated. For example, nerve transit times or distributions of transit times can be estimated for a plurality of nervous system locations such as Brodmann areas. Comparison of estimated transit times or distributions thereof between reference values or other values from the same structure can be used to assess specimen health.

18 Claims, 4 Drawing Sheets

(56) References Cited

U.S. PATENT DOCUMENTS

| | | |
|---|---|---|
| 7,881,878 B2 | 2/2011 | Burrus et al. |
| 2009/0010517 A1 | 1/2009 | Basser et al. |

OTHER PUBLICATIONS

Ikeda ("the relationship between nerve conduction velocity and fiber morphology during peripheral nerve regeneration", Brain and Behavior, 2012, 2(4):382-390) (Year: 2012).*

Nucifora et al. ("Diffusion-Tensor MR imaging and tractography: exploring brain microstructures and connectivity", Radiology; vol. 245, No. 3, 2007) (Year: 2007).*

University of Houston ("Moment statistics", statistics and probability, 2000) hereinafter "UH" (Year: 2000).*

Alexander et al., "Orientationally invariant indices of axon diameter and density from diffusion MRI," *NeuroImage*, 52:1374-1389 (2010).

Ritchie, "On the relation between fibre diameter and conduction velocity in myelinated nerve fibres," *Proceedings—Royal Society, Biological Sciences*, 217:29-35 (1982).

Barazany et al., "In vivo measurement of axon diameter distribution in the corpus callosum of rat brain," *Brain*, 132:1210-1220 (2009).

Assaf et al., "AxCaliber: A Method for Measuring Axon Diameter Distribution from Diffusion MRI," *Magnetic Resonance in Medicine*, 59:1347-1354 (2008).

Sherbondy et al., "MicroTrack: An Alogrithm for Concurrent Projectome and Microstructure Estimation," Medical Image Computing and Computer-Assisted Intervention, 183-190 (2010).

Deboy et al., "High resolution diffusion tensor imaging of axonal damage in focal inflammatory and demyelinating lesions in rat spinal cord," *Brain*, 130:2199-2210 (2007).

Westerhausen et al., "Functional Relevance of Interindividual Differences in Temporal Lobe Callosal Pathways: A DTI Tractography Study," *Cerebral Cortex*, 19:1322-1329 (2008).

Whitford et al., "Predicting inter-hemispheric transfer time from the diffusion properties of the corpus callosum in healthy individuals and schizophrenia patients: A combined ERP and DTI study," *NeuroImage*, 54:2318-2329 (2011).

Nucifora et al., "Diffusion-Tensor MR Imaging and Tractography: Exploring Brain Microstructure and Connectivity," *Radiology*, 245:367-384 (2007).

Akter et al., "Diffusion Tensor Tractography in the Head-and-Neck Region Using a Clinical 3-T MR Scanner," *Academic Radiology*, 16:858-865 (2009).

Waxman, "Determinants of Conduction Velocity in Myelinated Nerve Fibers," *Muscle & Nerve*, 3:141-150 (1980).

Paus, "Growth of white matter in the adolescent brain: Myelin or axon?" *Brain and Cognition*, 72:26-35 (2010).

Chung et al., "Principles and Limitations of Computational Algorithms in Clinical Diffusion Tensor MR Tractography," *American Journal of Neuroradiology*, 32:3-13 (2011).

Van Gelderen et al., "Evaluation of Restricted Diffusion in Cylinders. Phosphocreatine in Rabbit Leg Muscle," *Journal of Magnetic Resonance*, 103:255-260 (1994).

International Search Report and Written Opinion from International Application No. PCT/US2012/055458, dated Dec. 21, 2012, 19 pages.

J.W. Clark, "The Origin of Biopotentials," in Medical Instrumentation: Application and Design, 3rd edition, edited by J.G. Webster, John Wiley and Sons, Inc., New York, NY Chap. 4, pp. 121-182, 1998.

Barazany et al., "In-vivo Measurement of the Axon Diameter Distribution in the Rat's Corpus Callosum," *Proc. Intl. Soc. Mag. Reson. Med.*, 16:567 (2008).

Saint-Amour et al., "Can whole brain nerve conduction velocity be derived from surface-recorded visual evoked potentials? A re-examination of Reed, Vernon, and Johnson (2004)," *Neuropsychologia*, pp. 1-7 (2005).

Fukuzaki et al., "The ability of line scan diffusion imaging method comparison with echo planner diffusion imaging," *International Society for Magnetic Resonance in Medicine*, abstract, p. 1833 (1999).

Pierpaoli et al., "Polyvinylpyrrolidone (PVP) water solutions as isotropic phantoms for diffusion MRI studies," Abstract 1414, *Proc Intl Mag Reson Med*, 17th Annual Meeting and Exhibition, Honolulu, Hawai'i (Apr. 18-24, 2009).

\* cited by examiner

MRI TRACTOGRAPHY BASED TRANSIT TIME DETERMINATION FOR NERVE FIBERS

CROSS REFERENCE TO RELATED APPLICATIONS

This is a continuation of U.S. patent application Ser. No. 14/345,219, deposited Jun. 16, 2014, which is the U.S. National Stage of International Application No. PCT/US2012/055458, filed Sep. 14, 2012, which was published in English under PCT Article 21 (2), which in turn claims the benefit of U.S. Provisional Application No. 61/535,851, filed Sep. 16, 2011. The prior applications are hereby incorporated by reference.

STATEMENT OF GOVERNMENT RIGHTS

This invention was made with government support under a contract awarded by the Department of Health and Human Services, National Institutes of Health. The government has certain rights in the invention.

TECHNICAL FIELD

The invention pertains to magnetic resonance methods and apparatus for estimating nerve signal transit time distributions.

BACKGROUND

Magnetic resonance imaging (MRI) has been used with a variety of specimens in clinical and other applications. In many examples, images are based on differences in the so-called $T_1$ and $T_2$ relaxation times in the specimen being imaged. In other examples, translational diffusion can be used as a relaxation mechanism that produces image contrast. While in some specimens, translational diffusion of spins is isotropic, in many important applications, specimens exhibit structural features that make isotropic translational diffusion unlikely. To evaluate diffusion anisotropies of a specimen, so-called diffusion tensor (DT) methods such as those described in Basser et al., U.S. Pat. No. 5,539,310, can be used. These methods typically involve the application of pulsed-gradient magnetic fields in several directions. By evaluating diffusion anisotropies resulting from restricted or hindered diffusion, structural anisotropies can be identified and imaged as desired.

A variety of specimen parameters can be obtained using DT methods. For example, evaluation of water diffusion in brain white matter can provide estimates of the trace of the diffusion tensor, an apparent diffusion coefficient, relative anisotropy, or a fractional anisotropy. Parameters such as these can be used to assess brain white matter, and similar properties can be estimated for other specimens.

One application of DT based structural determination is DT-tractography that permits evaluation of the orientation of anisotropic structures throughout a specimen. Some DT-based tractographic methods are described in, for example, Burrus et al., U.S. Pat. No. 7,881,878, and Mori and van Zijil, "Fiber tractography: principles and strategies—a technical review," NMR Biomed. 15:468-480 (2002), both of which are incorporated herein by reference. One important application of DT tractography is the tracking of nerve fibers although the orientation of other elongated or otherwise anisotropic structures in biological and non-biological samples can be similarly investigated. While these tractography-based specimen evaluations can provide helpful structural information, they often do not provide information that is otherwise targeted to specimen properties of interest.

SUMMARY

According to representative methods, a path along a specimen structure is established based on a direction of a diffusion tensor principal axis at a plurality of locations along the path. A geometrical characteristic of the specimen structure is estimated along the established path at a plurality of path locations based on identification of a restricted diffusion direction, and contributions to a specimen function for the plurality of path locations are estimated based on the geometrical characteristic. A specimen functional value is estimated based on the contributions. In some examples, the specimen structure is a nerve fiber bundle, and the specimen functional value is a nerve signal transit time or a nerve signal transit time distribution associated with nerve signal propagation in the fiber bundle. In some examples, the estimated geometrical characteristic is a cross-sectional area associated with one or more fibers of the nerve fiber bundle, or a linear dimension associated with a fiber cross-section such as a diameter or an effective diameter of the fiber cross section, wherein the effective diameter is defined as a length corresponding to a diameter of a circle having an area that is substantially the same as the cross-sectional area. In some examples, the geometrical characteristic of the specimen structure along the established path is estimated based on a set of translational diffusion-weighted magnetic resonance signals associated with a plurality of diffusion-weighted field strengths and a plurality of diffusion-weighted field directions. In further examples, a signal portion in the set of signals is identified as corresponding to restricted diffusion, and a length associated with restricted diffusion is identified. In some examples, the set of field strengths is associated with a plurality of b-values of applied pulse field gradients. In representative examples, the specimen characteristic is a transit time, a transit time distribution, an electrical resistance, or a flow resistance along the path, and the cross-section is determined based on at least one of hindered or restricted diffusion in the specimen at a plurality of path increments. In typical examples, the cross-section is determined based on at least one of hindered or restricted diffusion in the specimen at a plurality of path increments. In representative examples, the specimen is nerve or muscle tissue, and the path is associated with a fiber or a bundle of fibers in the tissue. In one example, the path corresponds to a nerve fiber or fiber bundle, and the specimen function is a nerve signal transit time estimated as proportional to fiber diameter.

According to representative methods, a set of translational diffusion-weighted magnetic resonance signals associated with a plurality of diffusion-weighted field strengths and a plurality of diffusion-weighted field directions is obtained for a sample. A path and a cross-section along the path associated with at least one restricted compartment of the sample is established using the set of signals. A specimen functional characteristic associated with the path and the cross section is estimated. In some examples, the set of signals is a set of image signals, and the path corresponds to an orientation of the restricted compartment. In other examples, a principal axis of a diffusion tensor is determined, and the path is selected based on the principal axis. In alternative examples, paths and cross-sections associated with two or more restricted compartments, two or more hindered compartments are determined from the set of signals, and respective functional characteristics are estimated. According to representative embodiments, the cross-section is a radius, diameter, length, width, cross-sectional area, or other value associated with size of the restricted compartment. In typical examples, signal portions of the set of signals corresponding to diffusion in the restricted compartment are associated with diffusion in an intra-axonal volume of the sample. In alternative examples, an estimate of a spin fraction associated with restricted translational diffusion associated with a nerve fiber is estimated.

Representative apparatus comprise a magnetic resonance imaging system configured to obtain and record a set of translational diffusion-weighted magnetic resonance signals associated with a plurality of diffusion-weighted field strengths and a plurality of diffusion-weighted field directions in a specimen, and a processor configured to estimate a path of a structure in the specimen and a cross-sectional parameter of the structure at a plurality of path locations based on restricted diffusion associated with the specimen, and determine a functional characteristic of the structure based on the path and the plurality of cross-sectional parameters. In some examples, a display is coupled to the processor and configured to display an image corresponding to the path and the specimen structure. In further examples, the display is further configured to display path increments. In some examples, the processor is configured to estimate the path based on at least one principal diffusion axis associated with the restricted compartment. In representative embodiments, the path is associated with a nerve fiber, a nerve fiber bundle, a muscle fiber, or a bundle of muscle fibers.

Methods of in vivo nervous system assessment include identifying nerve pathways between a plurality of nervous system locations, and establishing transit time moments between at least some of the nervous system locations based on the identified nerve paths and a distribution of nerve fiber radii along the paths. In some examples, the plurality of nervous system locations includes a plurality of Brodmann areas. In additional examples transit time moments between a plurality of locations are compared, and an assessment is provided based on the comparison.

These and other features of the disclosed technology are set forth below with reference to the accompanying drawings.

DETAILED DESCRIPTION

Figure 1:
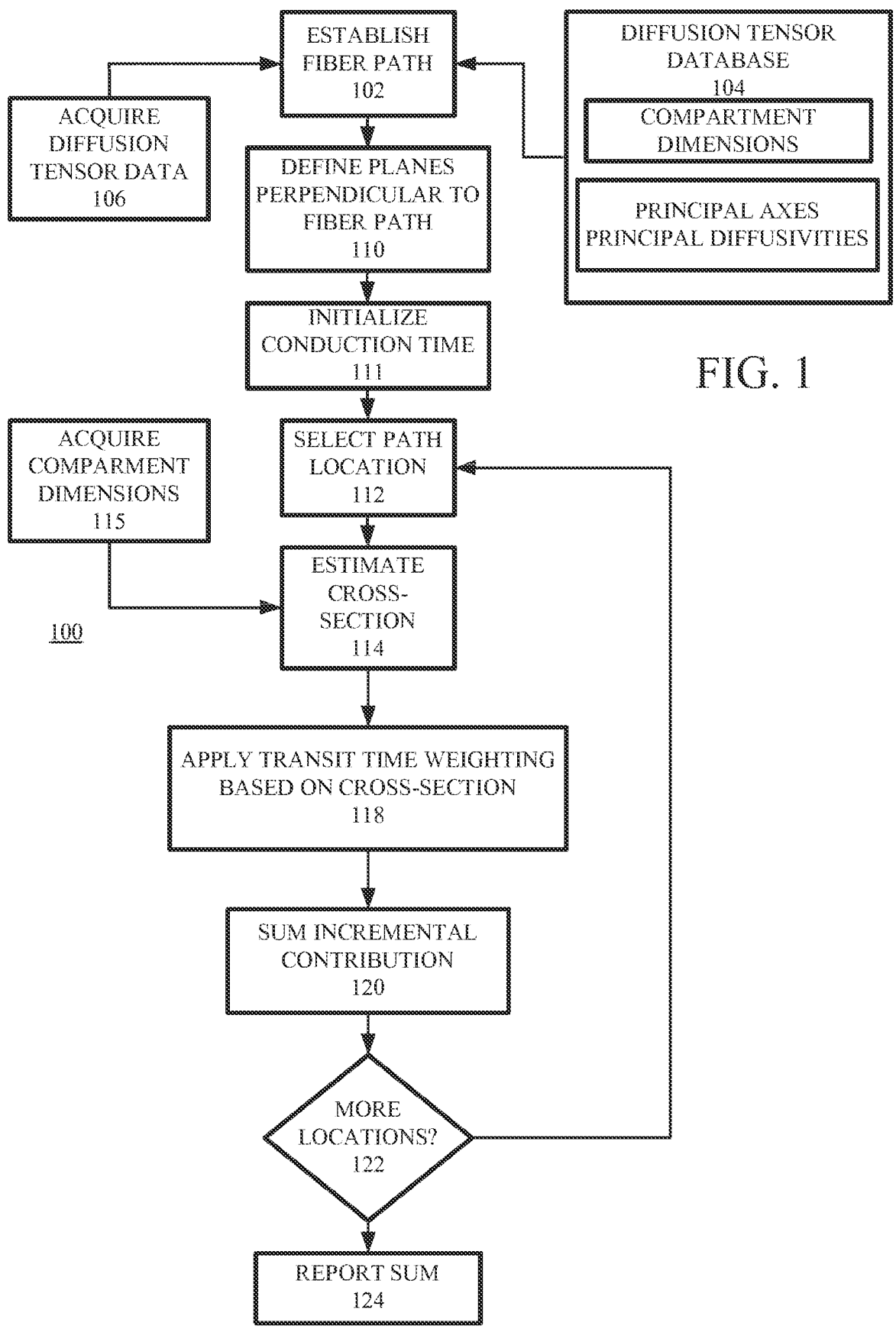
FIG. 1 is a block diagram illustrating a representative method of estimating nerve transit times based on axon paths and nerve fiber cross-sectional diameters.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

While the disclosed methods and apparatus can be applied to a variety of specimens, particularly specimens that exhibit anisotropic diffusion, for convenient explanation, examples described herein are generally based on measurements of nerve fibers, fiber bundles, brain white matter, and related structures. These examples are of practical importance. For example, magnetic resonance (MR) images of specimens exhibiting anisotropic translational diffusion such as brain white matter can be used in the diagnosis and therapy of a variety of disorders as well as the assessment of normal and abnormal brain development, degeneration, and aging. In addition to the evaluation of neural white matter (which can include multiple fiber orientations), other normal and pathologic tissues can be evaluated. Representative tissues include ischemic tissues and tissues associated with cerebral edema, cerebral hematoma, cerebral neoplasm, cerebral metastases. Tissues can be associated with neurodegenerative diseases such as stroke, multiple sclerosis, Alzheimer's disease, and Huntington's chorea. Evaluation of the efficacy of drugs and other treatments can be based on such path-based functional estimations as described herein. Other applications include neonatal screening and drug screening, as well as other clinical and industrial applications. In some examples, assessments of other fibrous tissues such as muscle can be obtained. A selected portion or portions of a specimen can be evaluated using these MR techniques, or a plurality of locations can be evaluated and an associated image assembled. For convenience in the following description, evaluation of one or a few specimen portions is described. These portions can correspond to volume elements (voxels) of an MR image. In typical examples, the disclosed methods and apparatus are directed to evaluation of in vivo specimens for diagnostic purposes, but other in vivo or in vitro specimens can be similarly evaluated or non-biological specimens can be evaluated.

For example, neurodegeneration such the axon demyelination associated with multiple sclerosis can be identified. A cancer treatment can be evaluated based on diffusion changes produced in response to the treatment. The efficacy of drugs and other treatments can be evaluated based on such structural evaluations. Identification and evaluation of restricted diffusion in anisotropic specimens can also be used in neonatal screening, drug screening, food processing, and other clinical and industrial applications. In other examples, fiber connectivity, white-matter integrity, and fiber-tracking in the vicinity of brain lesions can be evaluated. The methods presented herein can generally be applied to the evaluation and characterization of other anisotropic specimens that exhibit hindered and restricted diffusion MR images are generally based on detection of a magnitude, phase, orientation, or other property of spins of one or more sample constituents. In some examples, a spatially varying magnetic field such as a pulsed-gradient magnetic field is applied to a specimen to produce a spatial variation in spin angular frequency, which results in a spatial variation in the phase of these spins. Spin encodings that make MR signals sensitive to net spin displacements are referred to as herein as diffusion-weighted spins, and such encodings are referred to as diffusion encodings. Typical pulse sequences for diffusion weighting are based on pairs of diffusion sensitizing gradients such as those of Stejskal-Tanner encoding. Diffusion-weighted MR signals and images are based on such diffusion-weighted spins produced by such pulse sequences. Diffusion-weighted MR signals can be obtained that are associated with isotropic or anisotropic translational diffusion. Such signals are referred to herein as "diffusion-weighted signals" and images based on such signals are referred to as "diffusion-weighted images. Representative diffusion weighted imaging methods are described in, for example, Basser, U.S. Pat. No. 5,539,310, which is incorporated herein by reference.

As noted above, the disclosed examples are generally described with reference to brain white matter. Brain white is anisotropic and occupies a substantial fraction of brain volume. Brain white matter is composed of ordered fascicles whose axons are surrounded by a complex extra-axonal environment containing astrocytes, glia, and extracellular matrix. Axons (nerve fibers) are structurally anisotropic as a function of position due to the extension of the axons along a local axis. Some axons have associated myelin sheaths, but small-diameter axons are typically not myelinated. The orientation of this local axis typically varies throughout a specimen, but in other anisotropic specimens a local axis or other anisotropy can be constant throughout the specimen. White matter can be locally anisotropic with respect to a local axonal axis, and MR signals obtained from white-matter specimens can reflect this anisotropy. In some specimens, axons are not locally aligned with respect to a single axis.

Diffusion-weighted (DW) MR signals can be associated with spin diffusion parallel to and perpendicular to a local axonal axis (or a distribution of local axes) in intra-axonal volumes and/or extra-axonal volumes. Diffusion of spin-labeled species such as water molecules can be associated with so-called "hindered" diffusion in an extra-axonal space, and "restricted" diffusion in an intra-axonal space. "Hindered" diffusion typically refers to tortuous diffusion around diffusion barriers but without confinement to a particular volume, and "restricted" diffusion typically refers to diffusion constrained to a volume defined by surrounding diffusion barriers. MR signals can include contributions associated with restricted diffusion in the extra-axonal space as well, and such contributions can be analyzed in addition to the MR signal contributions associated with intra-axonal restricted diffusion. The evaluation of hindered and restricted compartments in various specimens, including the estimation of compartment shapes and dimensions as well as distributions of such shapes and dimensions is described in Basser et al., U.S. Pat. No. 7,643,863, which is incorporated herein by reference.

In diffusion tensor imaging (DTI), diffusion tensor values for some or all voxels of a specimen can be obtained, and the diffusion tensor can be represented based on its eigenvalues (principal diffusion coefficients) with respect to principal axes of diffusion. In this way, the diffusion tensor in some or all voxels can be represented as a spatially varying ellipsoid having axis lengths corresponding to the principal diffusivities and orientations associated with the principal axes. In the evaluation of elongated structures such as fiber bundles, a direction of the longest axis of this ellipsoid is typically associated with an orientation of a fiber bundle. The directionality (i.e., elongation) of the diffusion tensor ellipsoid can be characterized by a fractional anisotropy FA which ranges from 0 (isotropic diffusion) to 1 (diffusion along only a single axis). This and other ways of characterizing directionality are described in, for example, Mukherjee et al., "Diffusion Tensor MR Imaging and Fiber Tractography: Theoretical Underpinnings," Am. J. Neuroradial. 29:632-641 (2008) and Wedeen et al., U.S. Pat. No. 6,614,226, both of which are incorporated herein by reference.

MRI evaluation of anisotropic specimens based on modeling of translational diffusion of spins can be briefly described as follows. Spins in anisotropic specimens typically can be associated with either a hindered compartment in which spins diffuse in three dimensions without substantial impairment or to a restricted compartment in which spin diffusion is confined in at least one direction due to specimen structure. An MR signal can be decomposed into signal portions associated with a hindered spin fraction and a signal portion associated with a restricted spin fraction. The signal portion associated with the hindered spin fraction typically exhibits Gaussian diffusion decay while the signal portion associated with the restricted spin fraction exhibits non-Gaussian decay. In the restricted compartment, diffusion along one or more axes can be assumed to be uncorrelated so that diffusion along these axes can be modeled independently. In some examples, diffusion in a restricted compartment can be modeled along some directions as hindered diffusion and associated with a Gaussian diffusion decay. For example, for spins confined within a cylindrical volume, diffusion along a cylinder axis can be modeled as hindered, while diffusion perpendicular to the cylinder axis is restricted and exhibits non-Gaussian diffusion decay. In some cases, the restricted compartments can be represented as an ensemble of different, similar, or identical dimensions but with different orientations. This modeling framework can also reflect exchange of spins between the restricted compartment and the hindered compartment, and a variety of diffusion models can be selected for modeling of the compartments based on, for example, MR signal-acquisition characteristics. This modeling framework can be referred to as a "composite hindered and restricted model of diffusion" (CHARMED).

DTI can determine the diffusion ellipsoid (i.e., principal axes and principal diffusion coefficients) in each voxel of interest. By associating the principal diffusion coefficient and the associated principal direction with fiber orientation, a fiber path through a specimen can be followed from voxel to voxel. In some examples, other specimen images or other information can be used in conjunction with the diffusion ellipsoid data to aid in tracking fiber from voxel to voxel. Fiber tracking (i.e., tractography) can be based on a variety of tracking algorithms. For example, fiber trajectories can be based on principal axis directions tracked from voxel to voxel in three dimensions based on the diffusion tensor in a local neighborhood, starting at one or more "seed" voxels. Fiber direction is mapped by following principal axis directions, and changes at voxel edges as principal axis directions change. In some examples, a local 3 voxel by 3 voxel volume is used in tracking, but larger neighborhoods can be used. Directional changes at any voxel boundary can be limited so as to reflect more likely specimen structures as large, abrupt directional changes are generally not present in most biological samples. In addition, tracking can be limited to voxels having suitably large values of FA as tracking based on voxels exhibiting lower anisotropies can tend to be less accurate. A variety of more sophisticated tracking methods can be used as well, including sub-voxel based tracking methods, probabilistic methods, and methods associated with selection of suitable seed voxels from which fiber tracking is to start. Representative methods are described in, for example, Chung et al., "Principles and Limitations of Computational Algorithms in Clinical Diffusion Tensor MR Tractography," Am. J. Neuroradiol. 32:3-13 (2011). The methods and apparatus described herein are not limited to any particular tractography method, and a particular method can be selected as convenient for any particular example.

Diffusion-based MR measurements can also be configured to provide dimensional data associated with hindered or restricted compartments. For example, diffusion-sensitizing pulse sequences based on pulsed gradient fields generally produce MR signals that decrease as a function of elapsed time between the gradients. However, spins that are confined so as to exhibit restricted diffusion can diffuse only to a compartment boundary so that signal decrease as a function of elapsed time is less that of spins that can diffuse freely. Thus, by evaluation of diffusion weighed MR signals as a function of time, size characteristics such as lengths, widths, diameters, and volumes of restricted and/or hindered compartments can be estimated as well as distributions of such size characteristics can be estimated. Representative methods are described in Basser et al., U.S. Pat. No. 7,643,863. DTI images are generally obtained by applying suitable magnetic field pulses along at least 6 non-collinear axes (typically, along as many as 30 non-collinear axes to increase signal to noise ratio) at a b-value that can be selected based on the specimen to be investigated, with typical values in a range of from about 500 s/mm$^2$ to about 1200 s/mm$^2$. For rectangular gradient pulses, $b=\gamma^2 G^2 \delta^2(\Delta-\delta/3)$, wherein $\gamma$ is gyromagnetic ratio, $G$ is magnetic field gradient magnitude, $\delta$ is gradient pulse duration, and $\Delta$ is gradient pulse temporal separation. In addition, an image is also acquired at a low b-value or a 0 b-value.

A representative method 100 of determining specimen properties based on tractographic measurements and size or size distribution estimations of hindered or restricted compartments is shown in FIG. 1. At 102, a path of one or more fibers, fiber bundles, or other structures in a specimen is estimated in one or more voxels. This path determination is conveniently provided based on voxel diffusion tensor estimates for a plurality of voxels that can be retrieved from a database 104 or calculated from acquired DT data at 106, or a combination thereof. The database 104 can include estimates of diffusion tensor principal axes and principal diffusivities associated with a plurality of specimen locations. In addition, the database 104 can include compartment size estimates associated with the diffusion tensor estimates as well as estimates of compartment size distributions. For example, a fiber bundle can include a plurality of fibers that are substantially aligned and have common principal axes, but also include fibers having a distribution of fiber diameters or cross-sectional areas. The database 104 can be provided with all of this information for use in subsequent processing steps, or the associated data can be generated and stored separately as needed.

A fiber or fiber bundle path can be associated with a path direction that indicates a local fiber orientation. At 110, a series of planes perpendicular to such a fiber or fiber bundle orientation along the fiber path is selected. For simplicity, the series of planes can be uniformly spaced along the fiber path, or a non-uniform spacing can be used. For path locations at which fiber or fiber bundle properties such as orientation, shape, or cross-section are rapidly varying, more closely spaced planes may be more useful. At 111, a fiber transit time value is initialized, and at 112 an initial path location is selected. For this path location, an associated cross-sectional dimensional parameter such as effective radius, area, or other dimension is estimated at 114. The estimate can be based on stored values of previously analyzed q-space MR data from a database such as the database 104, or an additional signal acquisition 115 can be initiated to establish compartment dimensions and a distribution of compartment dimensions at the selected location. As mentioned above, fiber tractography data and cross-sectional data can be extracted based on application of a series of MR pulse sequences followed by suitable analysis of the detected signals.

MR signals associated with diffusion can be produced using a pulsed field gradient (PFG) sequence that is typically used in so-called q-space MRI, but other pulse sequences can be used. In q-space MRI, a sample portion is situated in a static magnetic field, typically for a duration long enough to permit some or all spins of one or more species in the sample portion to align with the static magnetic field. A radiofrequency (RF) pulse generator is configured to produce an RF pulse (a so-called $\pi/2$-pulse) so that specimen spins are rotated into a plane perpendicular to the static magnetic field. A gradient pulse described by a gradient-pulse waveform $G(t)$ associated with a magnetic field gradient $G_0$ having an effective pulse duration $\delta$ is applied to produce a spin rotation of $q=(1/2\pi)\gamma G_0 \delta$, wherein $\gamma$ is a gyromagnetic ratio and $q$ is the magnitude of $q$. In some examples, the duration $\delta$ is sufficiently short so that spin displacements during the application of the gradient-pulse waveform $G(t)$ are small compared to spin displacements that occur during a diffusion time $\Delta$ after which spin diffusion is measured, and spin diffusion during the gradient-pulse duration $\delta$ can be neglected. The magnetic field produced by application of the gradient-pulse waveform $G(t)$ is a function of spatial coordinates, and application of the gradient pulse produces a spatially tagged spin distribution. During the diffusion time Δ, the spin-labeled species move (by, for example, diffusion) and the spatially tagged spin distribution changes. Another RF pulse (a so-called π-pulse) is applied followed by a reapplication of the PFG. The combination of the π-pulse and the PFG tends to reverse the spatial tagging of spins, but does not reverse changes in the spatial spin distribution associated with diffusion or other spin displacements. Therefore, the MR signal obtained after application of this sequence can be associated with spin diffusion or other spin displacements in the specimen. Many other pulse sequences can be used, and other examples are described in, for example, P. Callaghan, *Principles of Nuclear Magnetic Resonance Microscopy* (Oxford University Press, 1991). In some examples, described in, for example, R. Kimmich, *NMR: Tomography, Diffusometry, Relaxometry* (Springer Verlag 1997), a diffusion sequence or "diffusion filter" can be applied before the imaging sequence.

If translational spin diffusion produces a 3-dimensional Gaussian displacement distribution and δ«Δ, then an MR signal produced using the PGF sequence can be expressed as:

$$|E(q)|=\exp(-4\pi^2 q^T D q \Delta),$$

wherein D is a diffusion tensor, and $q^T$ is the transpose of q, i.e., $q^T$ is a row vector corresponding to the column vector q. By application of a series of gradient pulses in different directions, estimates of the values of the elements of the tensor D can be obtained. Depending on magnitudes of the pulse-gradient duration δ and the diffusion time Δ, an effective diffusion time $\Delta_{eff}=\Delta-\delta/3$ can be used in the above expression instead of the diffusion time Δ. A similar expression can be obtained for MR signals in isotropic specimens. In some examples, expressions for MR signals can be expressed in terms of a so-called "b-value," wherein b is proportional to a product of $(\gamma G_0 \delta)^2$ and the effective diffusion time.

Fiber functional properties associated with the selected path increment can be estimated at 118 by selecting a suitable value based on fiber cross section or other compartment parameter at the selected location. For example, nerve signal propagation speed v in nerve fibers can be expressed as a function of fiber cross-section diameter D, i.e., v=v(D), and a transit time associated with signal propagation at the selected path location can be estimated based on the cross section and the incremental path length ΔL. For example, for a selected path element, an incremental transit time contribution ΔL/v(D) is summed with values associated with other path increments at 120. In some examples, cross-sectional planes are equally spaced and transit time contributions can be summed with a common path length ΔL. However, for unevenly spaced planes, transit times are based on fiber cross-sectional diameter as well as a fiber length increment associated with the selected location, and contributions can be expression as $\Delta L_i/v(D_i)$, wherein $\Delta L_i$ is an incremental length of an $i^{th}$ path element, and $D_i$ is an associated cross-sectional area. In addition to estimating transit time for the incremental path at the selected location, a transit time distribution based on a distribution of fiber cross-sections can be similarly obtained. For example, a particular path location can be associated with a distribution P (D) of fiber cross-section diameters, and a transit time distribution estimated based on the distribution and the propagation speed for each cross-sectional area. A fiber bundle transfer function can be estimated based on a product of transfer functions for the path increments, and the incremental transfer functions estimated as Laplace or Fourier transforms of path increment impulse response. At 122, if additional path locations are to be considered, an additional path location is selected at 112, and process steps are repeated. If consideration of the entire path (or a selected portion of a path) is complete, a sum value or an associated transform is reported at 124.

Transit times associated with path increments can be estimated based on measured or predicted relationships between conduction velocity and path increment cross-sectional dimensions. For example, in myelinated peripheral nerve fibers, conduction velocity has been shown to be proportional to fiber diameter when fiber diameter and internodal length are proportional to each other. At some small fiber diameters, internodal length may cease to be proportional to fiber diameter, and conduction velocity may be substantially less. For central nervous system fibers, the proportionality between diameter and intermodal length may extend to smaller diameters due to a different myelination structure. Transit time dependence of fiber diameter and internodal separation is discussed in detail in Ritchie, "On the relation between fibre diameter and conduction velocity in myelinated nerve fibres," Proc. R. Soc. Lond. B 217:29-35 (1982), which is incorporated herein by reference.

In the example of FIG. 1, transit times (or a transit time distribution) associated with varying cross-sectional areas or other structural characteristics that vary along a fiber path are estimated. However, in other examples, other path varying properties of a fiber-like or fiber-bundle-like structures can be estimated. For example, flow characteristics such as fluid resistance can be estimated based on fiber cross sectional area, total restricted or hindered volume, viscosity as a function of path length, or varying spin density along a path of a fiber or fiber bundle. For laminar flow in tube, an incremental fluid resistance is proportional to a ratio of a product of incremental length and viscosity to a fourth power of tube radius. Thus, based on a path determination and an estimation of restricted compartment radius (or other cross sectional parameters), a total fluid resistance can be obtained as sum of such increments. Thermal characteristics of such structures can be similarly obtained. Additional electrical characteristics of fibers or other elongated structures such as resistance, capacitance, mutual and self-inductance, and propagation delay can be estimated based on conductivity, area, and other parameters that vary along a path length. For example, a total electrical path resistance can be estimated as a sum of a product of incremental path lengths and path varying ratios of p/A, wherein ρ is resistivity and A is cross-sectional area. Using tractographically obtained paths and path-varying geometrical and compositional characteristics of a specimen, specimen functional properties can be estimated, even those for which direct determination of a path is difficult or impossible.

The method of FIG. 1 is provided as a representative example. Typically, a functional characteristic and a distribution of such a functional characteristic for a structure can be represented as an integral of contributions along a path. For example, for nerve fibers, propagation speed V can be expressed as $V=kR_0$, wherein k is a constant and $R_0$ is an inner diameter of a myelinated axon. An axon radius distribution p(R) can then be expressed as a function of propagation speed V, p(V). Accordingly, mean speed can be estimated as:

$$\langle v \rangle = \int V p(V) dV.$$

Thus, mean speed is proportional to mean radius, $\langle v \rangle = k \langle R_0 \rangle$. Higher order moments can be similarly obtained as:

$$\langle v^n \rangle = \int V_n p(V) dV = k \langle R^n \rangle.$$

A distribution of fiber transit times can be obtained from a distribution of transit speeds along a path:

$$p(\tau) = p(L/V) = p(L/kR_0) = \frac{kR_0^2}{L} p(R_0).$$

A mean transit time can be determined as $$\langle \tau \rangle = \int \tau p(\tau) d\tau$$

and higher order moments determined as $$\langle \tau^n \rangle = \int \tau^n p(\tau) d\tau.$$

Thus, using a distribution of axon radii determined based on restricted diffusion, an MRI-based path determination, and a proportionality constant k, mean and other moments of a transit time distribution can be estimated. The constant k may be difficult to estimate, and various ratios including moment ratios can be used for assessment so that dependence of k is eliminated. In one example, a first moment of a velocity distribution can be scaled as:

$$\frac{\langle V \rangle}{\sqrt{\langle (V - \langle V \rangle)^2 \rangle}}$$

and explicit dependence on k is eliminated.

Estimated transit time distributions, mean transit time, and other moments can be used to indicate nerve pathway performance for the assessment and evaluation of disease and disabilities of the central nervous system and the peripheral nervous system. In some cases, multiple nerve pathways can be evaluated in this way to provide a transit time matrix for connected regions. In one example, inter-region transit times for one or more Brodmann areas can be determined based on evaluation of selected pathways between these areas. For example, mean transit times $\tau_{ij}$ between $i^{th}$ and $j^{th}$ Brodmann regions can be arranged as a transit time matrix. Similar transit time moment matrices can also be provided for higher order moments. Unconnected areas can be represented by leaving a blank in such matrices.

Figure 2:
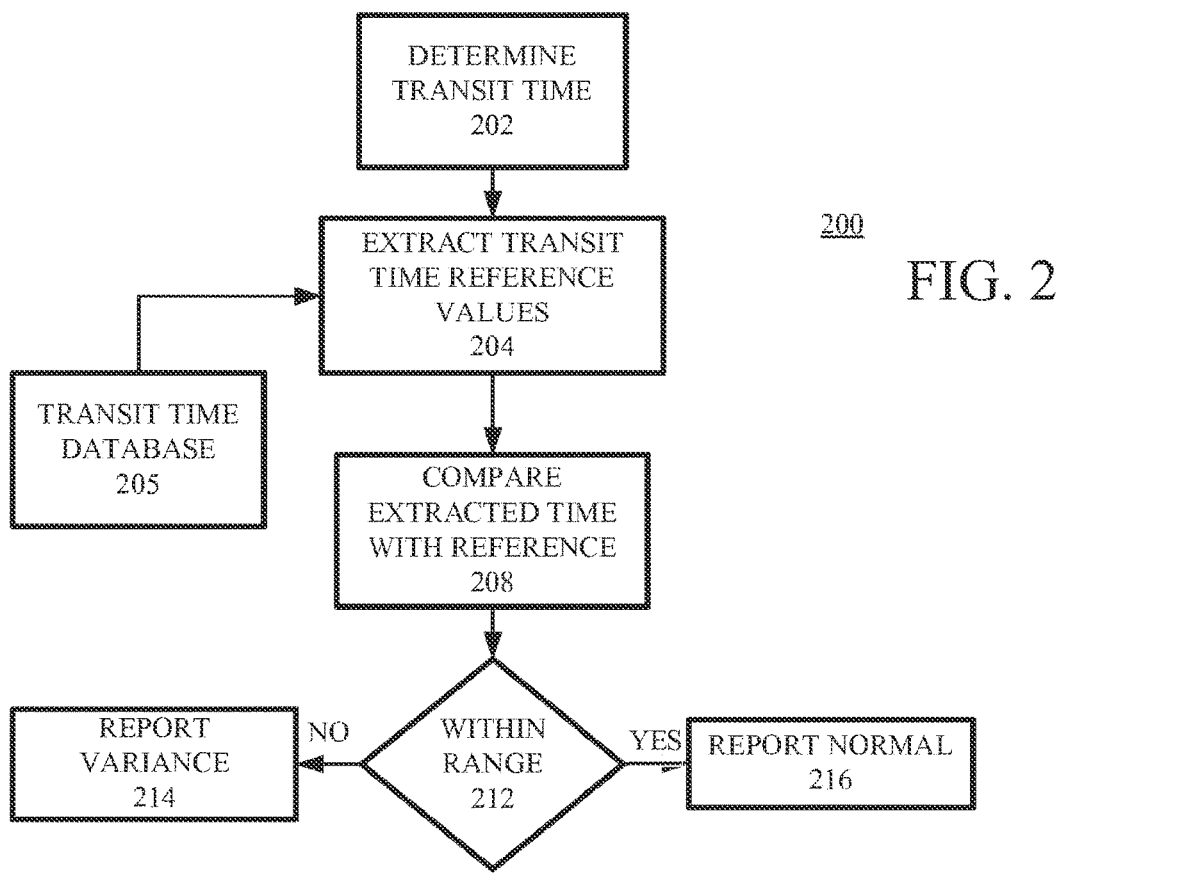
FIG. 2 is a block diagram illustrating a representative method of assessing a specimen based on estimated axon transit times.

Referring to FIG. 2, a method of specimen evaluation based on transit times includes determining one or more transit times at 202. Transit times can be obtained for various portions of a specimen or using a variety of measurement conditions. In addition, a total measurement time can be obtained for a specific structure or portions thereof, and evaluation of a structure can be based on one or more portions. At 204, corresponding reference values are retrieved from a database 205. The reference values or ranges thereof can be associated with a variety of normal or abnormal specimen conditions such as, for human tissue specimens, a variety of tissue types, patient age, gender, and one or more diseases along with a typical range of normal values. At 208, one or more measured values are compared with reference vales. At 212, a determination is made as to whether the measured values are within normal ranges, or within ranges associated with one or more abnormal specimen conditions. At 216, a report that values are within normal ranges is provided while at 214 variances from normal values are reported. In some examples, a particular range associated with a specimen abnormality can be used for comparison, and based on the comparison, a likelihood that the specimen has such an abnormality can be reported.

Figure 3:
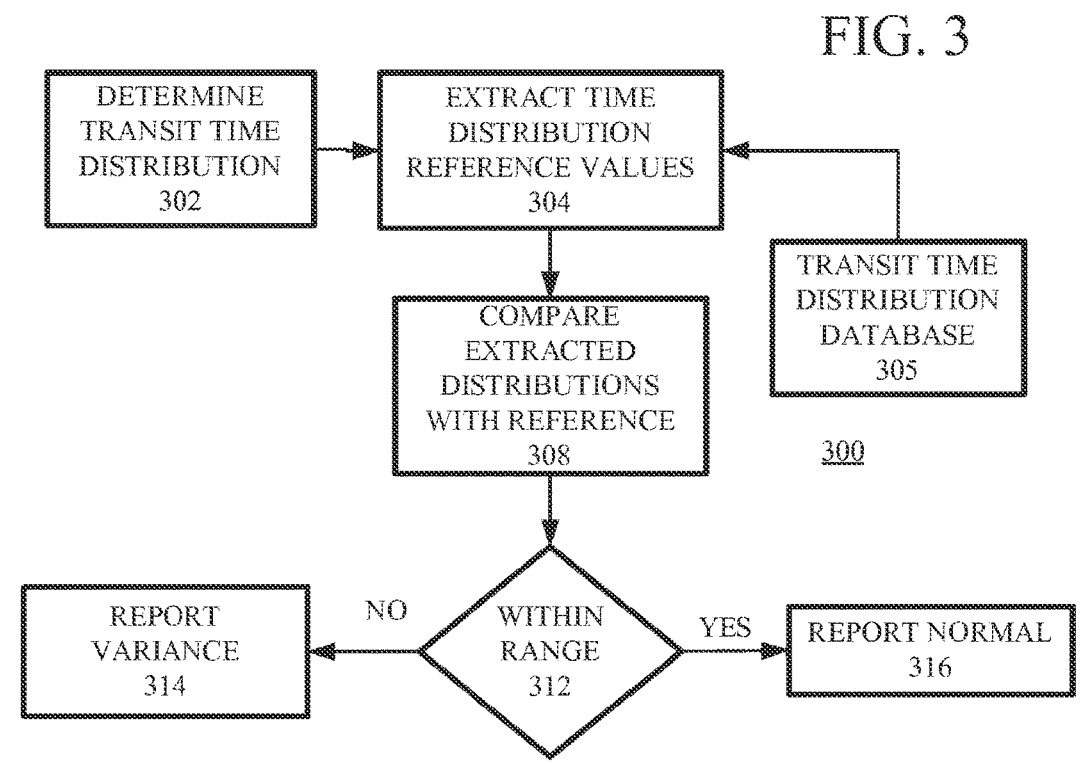
FIG. 3 is a block diagram illustrating a representative method of assessing a specimen based on estimated axon transit time distributions.

FIG. 3 illustrates a method 300 similar to that of FIG. 2 but based on one or more transit time distributions associated with distributions of hindered or restricted diffusion compartments in a specimen along one or more paths. At 302, a transit time distribution is estimated based on structure path and diameter along the path. At 304, reference values are extracted from a database 305, and compared with the extracted reference values at 308. The measured and reference values are compared at 312, and based on the comparison, the measured values are reported as within a normal range at 316 or reported as varying from a normal range at 314.

The methods of FIGS. 2-3 are based on comparisons of measured specimen values with one or more stored values obtained based on evaluation of other specimen so as to establish standard and abnormal ranges. In other examples, transit times or transit time distributions can be estimated as shown in FIG. 1, and compared with measured values. Such a comparison can aid in assessment as any discrepancy between the estimated and measured values can be indicative of an unexpected or unexplained specimen condition, or failure to establish a suitable specimen structure path. Comparisons can also be with respect to previous estimates for a selected specimen or patient, so the efficacy of a treatment or progress of a disease can be tracked.

Figure 4:
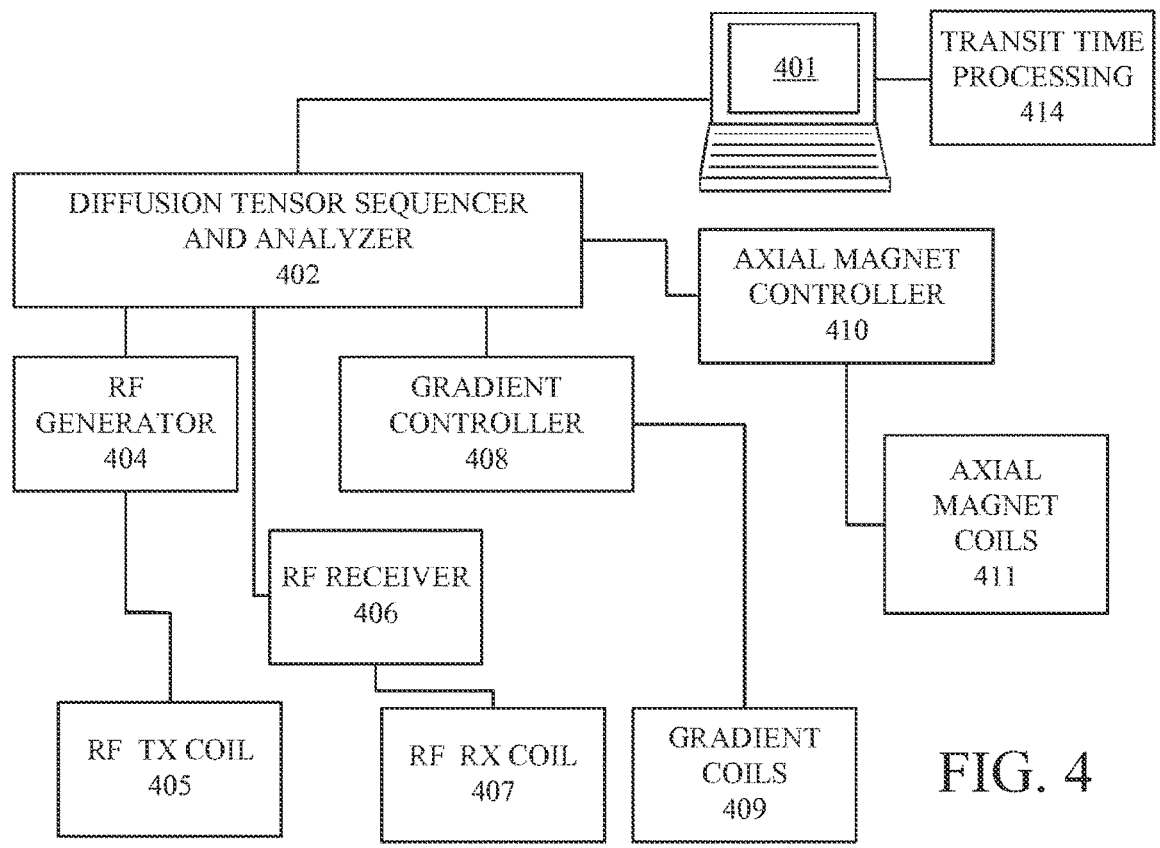
FIG. 4 is a schematic block diagram of a representative magnetic resonance (MR) apparatus configured to apply MR pulses to a specimen, determine one or more principal diffusivities and principal axes, and estimate transit times in nerve fibers or fiber bundles.

FIG. 4 is a schematic illustration of a representative apparatus configured to provide specimen functional characteristics such as fiber bundle transit times using MR-based specimen analysis. As shown in FIG. 4, the MR apparatus includes a personal computer 401 or other computing device such as a laptop, workstation, or tablet computer configured to select one or more MR pulse sequences for the acquisition of diffusion tensor based images. The computer 401 can provide a user interface for controlling data acquisition, analysis, and storage. A diffusion tensor (DT) sequence/analyzer 402 is coupled to the computer 401 and is configured to establish suitable pulse sequences including numbers of pulse, pulse duration, pulse strength, and pulse orientations, including gradient pulse orientations. The DT sequencer 402 is coupled to an RF generator 404 that can produce RF pulses that are coupled into specimen by an RF transmit coil 405. An RF receiver 406 is coupled to detect signals from the specimen via an RF receive coil 407, and a gradient controller 408 is configured to apply gradient magnetic fields to the specimen with a plurality of gradient coils 409. An axial magnetic field controller is coupled to one or more axial magnet coils 411. The DT sequencer 402 is configured to apply the selected fields in a suitable sequence and to process the received data to determine specimen properties of interest. Typically pulsed-field gradients ("PFGs") are applied along a plurality of directions to obtain diffusion-weighted images or MR signals. These MR signals can be processed with computer executable instrumentation in a dedicated processor, in the DT sequencer 402, or at the computer 401. In some examples, computer executable instructions for processing of acquired MR data to obtain transit times/distributions are provided at 414.

Figure 5:
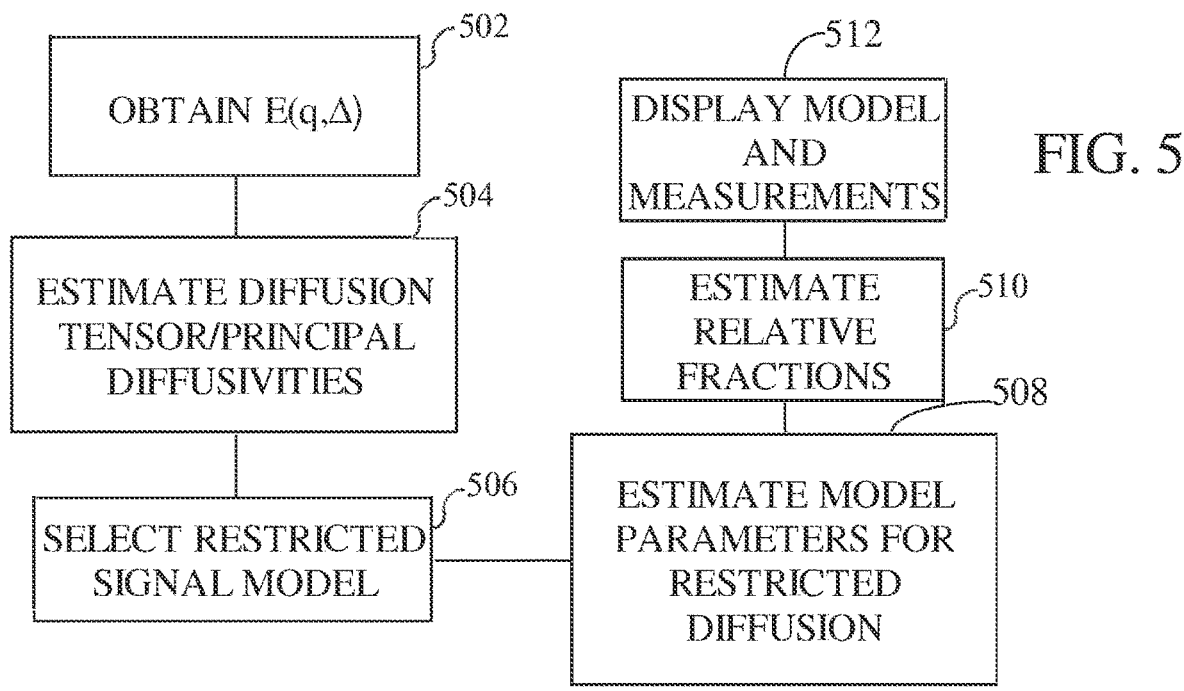
FIG. 5 is a schematic block diagram illustrating a method for modeling magnetic resonance (MR) signals and extracting model parameters associated with hindered and/or restricted spin diffusion in anisotropic specimens.

A representative method 500 of acquiring diffusion-based MR data is illustrated in FIG. 5. In a step 502, MR signals $E(q, \Delta)$ are obtained for variety of q-values and q-directions. Signals can be obtained by fixing a magnitude and duration of an applied pulsed-gradient magnetic field or effective magnitude of other spin-encoding magnetic field (i.e., fixing q), and varying the direction in which the encoding field is applied. After signals associated with the various directions are obtained, the q-value is changed and another series of signals at the various directions is obtained. Alternatively, signals can be obtained by fixing the direction of the applied encoding field and varying q. The direction of the encoding field can then be changed, and signals as a function of q can be obtained. Other signal acquisition sequences can be used.

After obtaining the MR signal E(q,Δ) for a variety of encoding field directions, model parameters associated with hindered spin diffusion are determined in a step 504. Typical model parameters determined in this step can include principal diffusivities $\lambda_{//}$, $\lambda_{\perp}$ and an orientation of the local axonal axis and can be based on diffusion tensor methods. A signal model for restricted diffusion perpendicular to the local axonal axis is selected in a step 506. Representative signal models include the expressions of Neumann and Callaghan described above and those described in P. van Gelderen et al., "Evaluation of restricted diffusion in cylinders. Phosphocreatine in rabbit leg muscle," J. Magn. Reson. B. 103:255-260 (1994). Model parameters associated with the selected model are obtained in step 508. Typical parameters include diffusion constants $D_{//}$ and $D_{\perp}$ for diffusion parallel and perpendicular to the local axonal axis and a cylinder radius. In a step 510, relative fractions of spins that exhibit hindered and restricted diffusion can be estimated. In a step 512, modeled signals can be computed and displayed with respect to measured signals, or compared with one or more baseline or control values associated with normal tissues or diseased tissues.

The method 500 of FIG. 5 shows steps performed in a specific order, but these steps can be performed in different orders, and model parameters for restricted and hindered signal components can be estimated in a common step or in a series of steps. Different models can be selected for other specimens, and the cylindrical model described herein is only a representative example.

Figure 6:
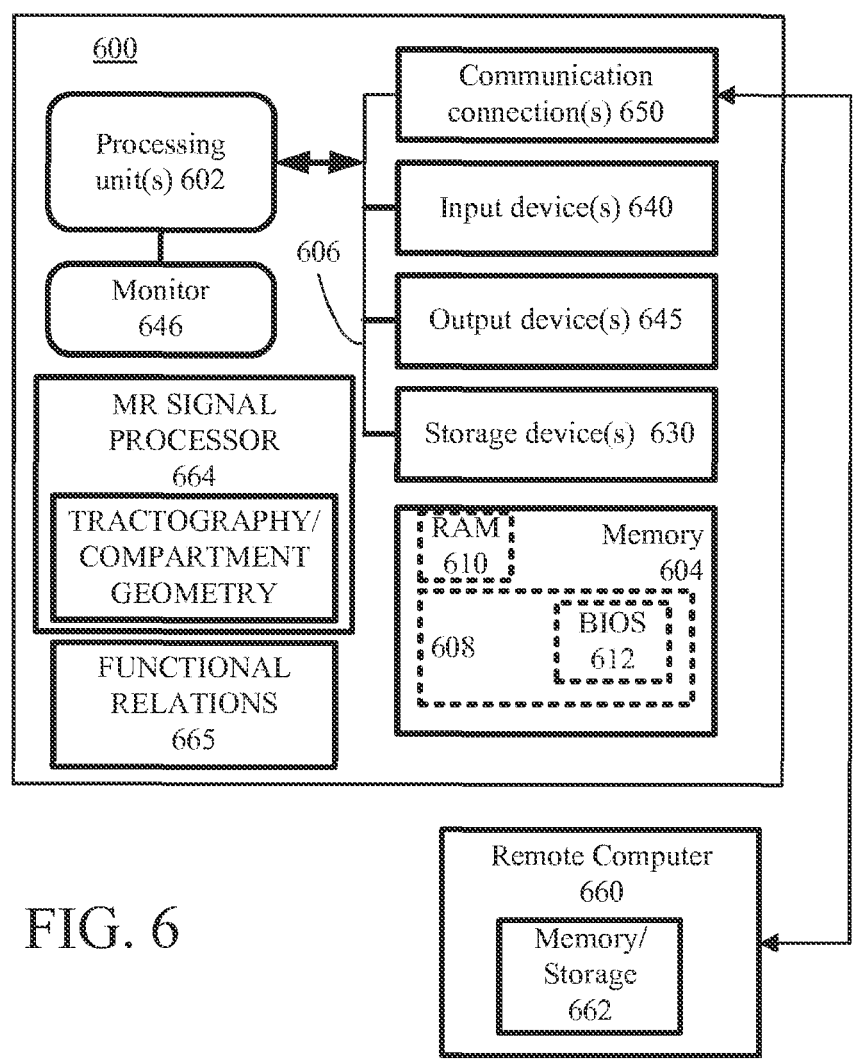
FIG. 6 is a schematic diagram of a representative computing environment for directing the acquisition and processing of MR data, and providing comparisons based on reference values.

FIG. 6 and the following discussion are intended to provide a brief, general description of an exemplary computing environment in which the disclosed technology may be implemented. Although not required, the disclosed technology is described in the general context of computer-executable instructions, such as program modules, being executed by a personal computer (PC). Generally, program modules include routines, programs, objects, components, data structures, etc., that perform particular tasks or implement particular abstract data types. Moreover, the disclosed technology may be implemented with other computer system configurations, including hand-held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices. In some examples, some or all portions of computing systems used to extract specimen paths from magnetic resonance diffusion tensor pulse sequences and to obtain information concerning hindered and restricted compartment dimensions can be co-located with an MR imaging system. In other examples, hardware can be configured to implement computer executable instruction for tractographic path determinations, compartment geometry extraction, and estimation of transit times or other specimen function based on data supplied from remote MR imaging systems.

With reference to FIG. 6, an exemplary system for implementing the disclosed technology includes a general purpose computing device in the form of an exemplary conventional PC 600, including one or more processing units 602, a system memory 604, and a system bus 606 that couples various system components including the system memory 604 to the one or more processing units 602. The system bus 606 may be any of several types of bus structures including a memory bus or memory controller, a peripheral bus, and a local bus using any of a variety of bus architectures. The exemplary system memory 604 includes read only memory (ROM) 608 and random access memory (RAM) 610. A basic input/output system (BIOS) 612, containing the basic routines that help with the transfer of information between elements within the PC 600, is stored in ROM 608.

The exemplary PC 600 further includes one or more storage devices 630 such as a hard disk drive for reading from and writing to a hard disk, a magnetic disk drive for reading from or writing to a removable magnetic disk, and an optical disk drive for reading from or writing to a removable optical disk (such as a CD-ROM or other optical media). Such storage devices can be connected to the system bus 606 by a hard disk drive interface, a magnetic disk drive interface, and an optical drive interface, respectively. The drives and their associated computer-readable media provide nonvolatile storage of computer-readable instructions, data structures, program modules, and other data for the PC 600. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices 530 including an operating system, one or more application programs, other program modules, and program data. A user may enter commands and information into the PC 600 through one or more input devices 640 such as a keyboard and a pointing device such as a mouse. Other input devices may include a digital camera, microphone, joystick, game pad, satellite dish, scanner, or the like. These and other input devices are often connected to the one or more processing units 602 through a serial port interface that is coupled to the system bus 606, but may be connected by other interfaces such as a parallel port, game port, or universal serial bus (USB). A monitor 646 or other type of display device is also connected to the system bus 606 via an interface, such as a video adapter. Other peripheral output devices, such as speakers and printers (not shown), may be included.

The PC 600 may operate in a networked environment using logical connections to one or more remote computers, such as a remote computer 660. In some examples, one or more network or communication connections 650 are included. The remote computer 660 may be another PC, a server, a router, a network PC, or a peer device or other common network node, and typically includes many or all of the elements described above relative to the PC 600, although only a memory storage device 662 has been illustrated in FIG. 6. The personal computer 600 and/or the remote computer 660 can be connected to a logical a local area network (LAN) and a wide area network (WAN). Such networking environments are commonplace in offices, enterprise-wide computer networks, intranets, and the Internet.

When used in a LAN networking environment, the PC 600 is connected to the LAN through a network interface. When used in a WAN networking environment, the PC 600 typically includes a modem or other means for establishing communications over the WAN, such as the Internet. In a networked environment, program modules depicted relative to the personal computer 600, or portions thereof, may be stored in the remote memory storage device or other locations on the LAN or WAN. The network connections shown are exemplary, and other means of establishing a communications link between the computers may be used.

In the example of FIG. 6, computer-executable instructions for processing MR signals are stored in a memory device 664. These instructions can be configured for path determinations via tractography compartment geometry determinations, and application of function relationships such as the dependence of nerve fiber transit time on fiber cross-section. Such instructions can be provided at a remote location as well, and executed remotely, or retrieved for local use. In addition, functional relationships associated with diffusion compartment geometries can be stored at 665. One or more processors can be coupled to one or more displays to as to show a specimen path with or without a specimen image, and functional contributions associated with one or more path increments can be displayed. In some examples, the path is shown alongside or in overlap with a specimen image.

Having described and illustrated the principles of the described technology with reference to the illustrated embodiments, it will be recognized that the illustrated embodiments can be modified in arrangement and detail without departing from such principles. For instance, elements of the illustrated embodiment shown in software may be implemented in hardware and vice-versa. Also, the technologies from any example can be combined with the technologies described in any one or more of the other examples. In view of the many possible embodiments to which the principles of the disclosure may be applied, it should be recognized that the illustrated embodiments are examples and should not be taken as a limitation on the scope of the disclosure. For instance, various components of systems and tools described herein may be combined in function and use. I therefore claim as the invention all subject matter that comes within the scope and spirit of the appended claims. Alternatives specifically addressed in these sections are merely exemplary and do not constitute all possible alternatives to the embodiments described herein.

I claim:

1. A method of evaluating magnetic resonance (MR) images to characterize, in vivo, a nervous system specimen, the method comprising:
    obtaining directions of an axis of a specimen structure of the nervous system specimen based on the MR images, the MR images and corresponding MR signals having been obtained by applying a plurality of MR pulse sequences to the nervous system specimen, in vivo;
    establishing a plurality of pathways at a plurality of locations along the specimen structure, the pathways corresponding to nerve pathways between a plurality of nervous system locations of the nervous system specimen, the plurality of pathways being established based on the obtained directions of the axis of the specimen structure at the plurality locations along the specimen structure;
    calculating, from the MR images, a distribution of radii of the specimen structure along the established pathways at the plurality of locations, the distribution of the radii of the specimen structure corresponding to a distribution of nerve fiber radii within the nervous system specimen;
    calculating transit time moments between at least two of the nervous system locations based on the established pathways and the distribution of radii of the specimen structure along the established pathways;
    arranging the transit time moments as a matrix of transit time moments;
    retrieving reference values for transit time moments from a database;
    comparing the transit time moments from the matrix to the reference values for the transit time moments; and
    reporting whether the transit time moments indicate an abnormality or fall within a normal range based on the comparison.

2. The method of claim 1, wherein the arranging the transit time moments as a matrix includes indicating unconnected specimen locations.

3. The method of claim 2, wherein unconnected specimen locations are indicated with blanks in the matrix of transit time moments.

4. The method of claim 1, wherein the transit time moments are mean transit times.

5. The method of claim 1, wherein the transit time moments are mean square transit times.

6. The method of claim 1, wherein the transit time moments are moments of order n, wherein n is an integer greater than 2.

7. The method of claim 1,
    wherein calculating the distribution of the radii of the specimen structure along the established pathways at the plurality of locations comprises calculating a respective radius of the specimen structure along for a plurality of the established pathways at the plurality locations, and
    wherein calculating the transit time moments comprises:
        calculating contributions to the transit time moments for the plurality of locations based on the respective radius of the specimen structure; and
        combining the calculated contributions along the respective pathways to determine the transit time moments.

8. The method of claim 7, wherein the pathways and the distribution of radii are associated with a nerve fiber, a nerve fiber bundle, an axon, an axon bundle, or brain white matter and the transit time moments correspond to mean transit times along the pathways and are determined as proportional to nerve fiber radii.

9. The method of claim 1, the method further comprising:
    prior to obtaining the directions of the axis of the specimen structure, applying the plurality of magnetic resonance (MR) pulse sequences to the nervous system specimen, in vivo, and obtaining the MR images based on the pulse sequences,
    wherein calculating the distribution of the radii of the specimen structure along the established pathways at the plurality of locations comprises calculating a respective radius of the specimen structure along for a plurality of the established pathways at the plurality locations, and
    wherein calculating the transit time moments comprises:
        calculating contributions to the transit time moments for the plurality of locations based on the respective radius of the specimen structure;
        combining the calculated contributions along the respective pathways to determine the transit time moments; and establishing the transit time moments by combining the calculated contributions along the respective pathways.

10. The method of claim 1, wherein the MR pulse sequences are diffusion-weighted pulse sequences and the MR images are based on at least one of restricted diffusion and hindered diffusion associated with the specimen structure.

11. The method of claim 10, wherein the pathways are based on one or more principal diffusion axes associated with restricted or hindered diffusion.

12. A magnetic resonance (MR) apparatus, the (MR) apparatus comprising:
  a plurality of field coils operatively coupled to expose, in vivo, a nervous system specimen to a plurality of diffusion-weighted pulse sequences;
  a receiver coil situated to receive MR signals from the nervous system specimen responsive to the plurality of diffusion-weighted pulse sequences; and
  a processor operable to:
    operate the MR apparatus to apply the plurality of diffusion-weighted pulse sequences to the nervous system specimen, in vivo, and to receive the MR signals;
    obtain MR images of the nervous system specimen based on the received MR signals;
    calculate a diffusion tensor for a plurality of voxels of the MR images;
    obtain directions of an axis of a specimen structure of the nervous system specimen based on a principal diffusion axis of the calculated diffusion tensor for each of the voxels;
    establish a plurality of pathways between a plurality of locations along the specimen structure, the established pathways corresponding to nerve pathways between a plurality of nervous system locations in the nervous system specimen based on the directions of the axis of the specimen structure at the plurality of locations;
    calculate cross-sectional parameters of the specimen structure at the plurality of the pathways based on the MR images;
    calculate transit time moments between at least two locations in the plurality of locations based on the established pathways and a distribution of the cross-sectional parameters, and
    arrange the transit time moments as a matrix.

13. The magnetic resonance apparatus of claim 12, wherein the arranging the transit time moments as the matrix includes indicating unconnected specimen locations.

14. The magnetic resonance apparatus of claim 12, wherein the transit time moments are mean transit times.

15. The magnetic resonance apparatus of claim 12, wherein the transit time moments are moments of order n, wherein n is an integer greater than 1.

16. The magnetic resonance apparatus of claim 12, wherein the cross-sectional parameters are cross-sectional areas or a linear dimensions associated with the cross-sections and contributions to the transit time moments for the plurality of nervous system locations are calculated based on the cross-sectional areas or the linear dimensions associated with the cross-sections and the calculated contributions along the respective pathways are combined to determine the transit time moments.

17. The magnetic resonance apparatus of claim 12, wherein contributions to the transit time moments are calculated for the plurality of locations along the pathways based on the distribution of the cross-sectional parameters and the calculated contributions are combined along the respective pathways to determine the transit time moments.

18. The magnetic resonance apparatus of claim 12, wherein the pathways the cross-sectional parameters are calculated based on at least one of restricted diffusion and hindered diffusion.

* * * * *